United States Patent [19]

Dorlars et al.

[11] Patent Number: 4,609,756

[45] Date of Patent: Sep. 2, 1986

[54] PROCESS FOR THE PREPARATION OF OPTIONALLY SUBSTITUTED CINNAMIC ACID IN THE PRESENCE OF A CATALYST

[75] Inventors: Alfons Dorlars, Leverkusen; Heinz U. Blank, Odenthal; Herbert Nordt, deceased, late of Leverkusen, by Hildegard Nordt, heiress; Viktor Trescher, Leverkusen, all of Fed. Rep. of Germany

[73] Assignee: Bayer Aktiengesellschaft, Leverkusen, Fed. Rep. of Germany

[21] Appl. No.: 784,283

[22] Filed: Oct. 4, 1985

[30] Foreign Application Priority Data

Oct. 13, 1984 [DE] Fed. Rep. of Germany ....... 3437634

[51] Int. Cl.$^4$ .............................................. C07L 63/64
[52] U.S. Cl. .................................... 562/495; 562/434; 562/478; 562/492; 549/434
[58] Field of Search .............. 562/495, 434, 478, 492; 549/434

[56] References Cited

U.S. PATENT DOCUMENTS 2,484,067 10/1949 Boese .................................. 562/495
2,554,528 5/1951 Fitzpatrick ......................... 562/495
2,585,223 2/1952 Caldwell ............................ 562/495

*Primary Examiner*—Paul J. Killos
*Attorney, Agent, or Firm*—Sprung Horn Kramer & Woods

[57] ABSTRACT

In the preparation of a cinnamic acid by reacting the corresponding benzaldehyde with ketene in the presence of a catalyst, the improvement which comprises using as the catalyst an iron and/or zinc salt of a mono- or di-carboxylic acid with 2 to 20 carbon atoms containing free carboxylic acid and/or anhydride, and then splitting the reaction product in the temperature range from 100° to 250° C. with an acid or basic catalyst.

11 Claims, No Drawings

PROCESS FOR THE PREPARATION OF OPTIONALLY SUBSTITUTED CINNAMIC ACID IN THE PRESENCE OF A CATALYST

The invention relates to a process for the catalytic preparation of optionally substituted cinnamic acid from the corresponding benzaldehyde and ketene and a catalyst of the group of iron and/or zinc salts of $C_2$–$C_{20}$-carboxylic acids containing amounts of the corresponding free carboxylic acids and/or anhydrides thereof.

In general, cinnamic acid is prepared industrially by the so-called Perkin process (Houben-Weyl, 4th edition, Volume 8, page 442 et seq. (1952); Org. React. I, page 210 to 265 (1942); and Ullmanns Encyclopädie der technischen Chemie (Ullmann's Encyclopaedia of Industrial Chemistry), 3rd edition, Volume 19, page 36 (1969)) from the corresponding benzaldehyde, acetic anhydride and an alkaline condensing agent.

The disadvantages of the Perkin process are the processing of large amounts of alkali metal acetates, large excesses of acetic anhydride and long reaction times.

It is also known that benzaldehyde and ketene can be reacted in the presence of potassium acetate to give a primary product from which about 22% of cinnamic acid is obtained (J.Am.Chem.Soc. 55, 275 (1933)). Under similar conditions, 30% of cinnamic acid and 70% of styrene were also obtained (Organic Synthesis, Volume I, 215 and 216 C. D. Hurd. C. L. Thomas, (1942)).

The reaction of benzaldehyde with ketene at 60° C. with the addition of sodium acetate and subsequent heating of the reaction product to the boiling point is known from Ind. Chem. 41, 768 (1949). Cinnamic acid is thereby obtained in a yield of 40%.

It is known from U.S. Pat. No. 2,484,067 (1969) that boron trifluoride can be used as a catalyst for this reaction. Cinnamic acid is thereby obtained in a yield of 42%.

In the known reactions of benzaldehyde with ketene in the presence of a catalyst, products with high styrene contents are formed.

A catalyst has been found for the reaction of optionally substituted benzaldehydes with ketene, which contains iron and/or zinc salts of mono- or di-carboxylic acids with 2 to 20 carbon atoms and amounts of the corresponding free carboxylic acids and/or anhydrides thereof.

Using such catalysts, it is possible to prepare optionally substituted cinnamic acids in high yields.

The iron and zinc salts to be employed according to the invention are preferably those of mono- or di-carboxylic acids of the formula

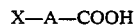

X—A—COOH in which
X denotes carboxyl or hydrogen and
A can denote a divalent radical which is derived from the group comprising saturated or unsaturated aliphatic hydrocarbons with 1 to 18 carbon atoms, cycloaliphatic hydrocarbons with 5 to 12 carbon atoms, araliphatic hydrocarbons with 7 to 18 carbon atoms or aromatic hydrocarbons with 6 to 12 carbon atoms and, if X represents a carboxyl group, also a single bond.

Saturated aliphatic hydrocarbons from which the divalent radicals are derived are here in general straight-chain or branched hydrocarbons with 1 to 18, preferably 1 to 12, carbon atoms. The following saturated aliphatic hydrocarbons may be mentioned as examples: methane, ethane, propane, butane, isobutane, pentane, isopentane, hexane, isohexane, heptane, isoheptane, octane, isooctane, nonane, isononane, decane, isodecane, undecane, isoundecane, dodecane and the isododecanes.

Unsaturated aliphatic hydrocarbons from which the divalent radicals are derived are here in general straight-chain or branched hydrocarbons with 2 to 18, preferably 2 to 12, carbon atoms and one or two, preferably one, double bond. The following unsaturated aliphatic radicals may be mentioned as examples, ethene, propene, butene, heptadecene, tert.-butylene and neopentylene.

Cycloaliphatic radicals are here in general cyclic hydrocarbon radicals with 5 to 12, preferably 5 to 8, carbon atoms. The following cycloaliphatic radicals may be mentioned as examples: cyclopentylene, cyclohexylene, cycloheptylene and cyclooctylene.

Araliphatic radicals are here in general radicals consisting of an alkylene part and an aromatic part. The alkylene part here can be a straight-chain or branched, saturated or unsaturated hydrocarbon radical with 1 to 12, preferably 1 to 6, carbon atoms and, if appropriate, one or two, preferably one, double bond. The aromatic part here can be, for example, a radical from the benzene series with 6 to 12 carbon atoms. The following araliphatic radicals may be mentioned as examples: benzylene and xylylene.

Aromatic radicals are here in general radicals from the benzene series with 6 to 12 carbon atoms. The following radicals may be mentioned as examples: phenylene, naphthylene and biphenylene, and toluylene and xylylene. The phenylene radical is preferred.

The iron and/or zinc salts to be employed according to the invention are particularly preferably those of monocarboxylic acids of the formula

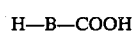

H—B—COOH in which
B can denote a divalent radical from the group comprising saturated aliphatic radicals with 1 to 12 carbon atoms, cycloaliphatic radicals with 5 or 6 carbon atoms, araliphatic radicals with 7 to 9 carbon atoms and aromatic radicals with 6 to 10 carbon atoms.

The iron and/or zinc salts of the following mono- or di-carboxylic acids may be mentioned as examples: acetic acid, propionic acid, butyric acid, isobutyric acid, valeric acid, isovaleric acid, pivalic acid, ethylmethylacetic acid, 2-ethyl-butanoic acid, dodecanoic acid, stearic acid, lactic acid, glycolic acid, hexahydrobenzoic acid, benzoic acid, phenylacetic acid, cinnamic acid, oxalic acid, malonic acid, succinic acid, adipic acid and phthalic acid.

According to the invention, the iron or zinc salts can be used as catalysts. It is of course also possible for mixtures of the iron and zinc salts to be used.

In the catalysts according to the invention, the iron and/or zinc salts contain amounts of the corresponding free carboxylic acids and/or anhydrides thereof. The catalysts preferably contain up to 80% by weight of the free carboxylic acids and/or anhydrides thereof. The catalysts particularly preferably contain 1 to 50% by weight of the free carboxylic acids and/or anhydrides thereof, based on the total catalyst.

The catalysts can be prepared by adding the corresponding amount of the carboxylic acid or anhydride to the neutral or basic salts, preferably the neutral salts, of zinc or 2- or 3-valent iron.

However, it is not absolutely necessary to add the carboxylic acids or the anhydrides, since the catalysts according to the invention with the content of carboxylic acids or anhydrides thereof can also be formed in situ.

The content of free carboxylic acids can be formed with the salts with water, small amounts of which are contained in the reaction medium, for example as adsorbed moisture on the surfaces of apparatuses or water of crystallization. Furthermore, acetic acid, which can enter the catalysts, is formed from water in the reaction with ketene.

However, it is preferable for the reaction according to the invention for the salts of iron or zinc with the corresponding content of free carboxylic acids and/or anhydrides thereof to be added at the start.

It is of course also possible to use iron and/or zinc salts of mono- or di-carboxylic acids which still have an acid content from their preparation process. The iron and zinc salts are in general prepared from the corresponding oxides or carbonates and the corresponding carboxylic acids.

If water, carboxylic acids and carboxylic acid anhydrides are excluded during the reaction, the reaction virtually does not start or proceeds unsatisfactorily.

The process according to the invention for the preparation of optionally substituted cinnamic acid by reaction of the corresponding benzaldehyde with ketene in the presence of a catalyst is characterized in that a catalyst from the group comprising iron and/or zinc salts of a mono- or di-carboxylic acid with 2 to 20 carbon atoms containing amounts of the corresponding free carboxylic acids and/or anhydrides thereof is used and the reaction product is then treated in the temperature range from 100° to 250° C. in the presence of an acid or basic catalyst.

The process according to the invention can be illustrated by the following equation:

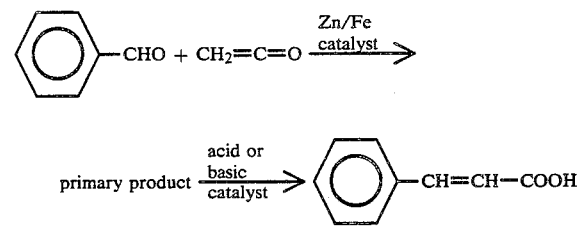

In the reaction of the optionally substituted benzaldehyde with ketene in the presence of the catalyst according to the invention, a primary product is formed, from which the cinnamaldehyde is prepared in the manner according to the invention.

The primary product is in general essentially an oligomeric polyester of β-hydroxy-β-phenyl-propionic acid with terminal acetyl or acetoxy groups and an average molecular weight of 1,000 to 1,500, and can be isolated as a light-colored, viscous product.

In the case of benzaldehydes with negative substituents, it is, however, also possible for the primary products to be in the form of β-aryl-β-propiolactones.

For the process according to the invention, however, it is not necessary to isolate the primary product. The reaction of the optionally substituted benzaldehyde with ketene and the subsequent reaction of the primary product are as a rule carried out as a one-pot reaction.

All the benzaldehydes which, on the basis of their reactivity, are possible can be used as optionally substituted benzaldehydes for the process according to the invention.

Preferred benzaldehydes for the process according to the invention are compounds of the formula

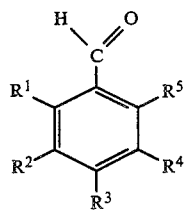

in which, preferably, one ortho-position is unsubstituted and $R^1$ and $R^5$ are identical or different and denote hydrogen, halogen, hydroxyl, nitro, lower alkyl, lower alkoxy or optionally substituted phenyl, it being possible for an aromatic ring to be fused onto two adjacent radicals, or it being possible for two adjacent radicals to be connected by the group

—O—CH$_2$—O—.

Halogen here in general denotes fluorine, chlorine, bromine or iodine, preferably chlorine or bromine.

Lower alkyl denotes, for example, a straight-chain or branched hydrocarbon radical with 1 to 6 carbon atoms. The following lower alkyl radicals may be mentioned as examples: methyl, ethyl, propyl, isopropyl, butyl, isobutyl, pentyl, isopentyl, hexyl and isohexyl.

Lower alkoxy denotes, for example, an alkyl ether radical with 1 to 6 carbon atoms. The following lower alkoxy radicals may be mentioned as examples: methoxy, ethoxy, propoxy, isopropoxy, butoxy, isobutoxy, pentoxy, isopentoxy, hexoxy and isohexoxy. The methoxy and ethoxy radical are preferred.

The phenyl radical can be optionally substituted. Examples of substituents which may be mentioned are: lower alkyl with up to about 6 C atoms, lower alkoxy with up to about 6 C atoms and halogen.

If an aromatic ring is fused onto two adjacent radicals $R_1$ to $R_5$, a naphthalene system, for example, is present.

If two adjacent radicals $R_1$ to $R_5$ are connected by the group —O—CH$_2$—O—, a methylene-dioxy-phenyl system, for example, is present.

Particularly preferred benzaldehydes are those of the formula

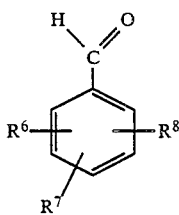

in which, preferably, one ortho-position is unsubstituted and $R^6$ to $R^8$ are identical or different and denote hydrogen, fluorine, chlorine, bromine, nitro, methyl, ethyl, methoxy, ethoxy or phenyl, it being possible for two adjacent radicals to be connected by the group

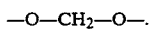
—O—CH$_2$—O—.

The following optionally substituted benzaldehydes may be mentioned as examples: benzaldehyde, o-, m- and p-fluorobenzaldehyde, o-, m- and p-chlorobenzaldehyde, o-, m- and p-bromobenzaldehyde, o-, m- and p-iodobenzaldehyde, 3-bromo-4-fluorobenzaldehyde, 2-chloro-6-fluorobenzaldehyde, 2,4-, 2,5-, 2,6- and 3,5-dichlorobenzaldehyde, 2,3,4-, 2,4,5-, 2,3,6- and 3,4,5-trichlorobenzaldehyde, pentachlorobenzaldehyde, o-, m- and p-tolylaldehyde, 3- and 4-ethylbenzaldehyde, 4-isopropyl- and 4-phenylbenzaldehyde, 4-butylbenzaldehyde, 2-, 3- and 4-methoxybenzaldehyde, 4-ethoxy-, 4-propoxy-, 4-butoxy- and 4-phenoxy-benzaldehyde, piperonal, 2,4-d-methoxy- and 3,4-dimethoxy-benzaldehyde, o-, m- and p-nitrobenzaldehyde, 4-acetoxybenzaldehyde, 4-hydroxy-benzaldehyde, 2-nitro-4-chlorobenzaldehyde, 2-nitro-4-bromobenzaldehyde, 2,4- and 2,6-dinitrobenzaldehyde, 4-methoxy-3-nitrobenzaldehyde, 4-methyl-2-fluoro-benzaldehyde, 4-methyl-2,3-dichlorobenzaldehyde, 4-methyl-3-nitrobenzaldehyde, 2,4,6-trimethyl-3,5-dinitrobenzaldehyde, 4'-chloro-4-formyl-biphenyl, 3-methoxy-2-, 3-methoxy-4- and 3-methoxy-6-nitro-benzaldehyde, 3,4,5-trimethoxybenzaldehyde, 1-naphthaldehyde, 2-naphthaldehyde and 4-chloro-naphthaldehyde.

The reaction of benzaldehyde is particularly preferred.

The optionally substituted benzaldehydes for the process according to the invention are known and can be prepared by known processes.

Gaseous ketene, which can be prepared, for example, by pyrogenic splitting of acetone or acetic acid on a chromium/nickel spiral (Houben-Weyl, Volume VII/4, page 68) is in general used for the process according to the invention, it also being possible for technical grade qualities, which may be contaminated, to be used.

In general 0.40 to 1.20 mols, preferably 0.50 to 0.96 mols, of ketene per mole of the optionally substituted benzaldehyde are employed for the process according to the invention.

In general 0.1 to 10 mol %, preferably 0.5 to 4 mol %, of the catalyst according to the invention, based on the benzaldehyde used, is employed for the process according to the invention.

The process according to the invention can be carried out with or without a solvent. In particular, in the reaction of benzaldehydes which are liquid under the reaction conditions, solvents can be dispensed with if attention is paid to good thorough mixing which can be ensured, for example, by carrying out the reaction with less than the equimolar amount (about 50-80% by weight of the theoretical amount) of ketene.

However, the process according to the invention is preferably carried out in the presence of solvents. Possible solvents for the process according to the invention are those which are inert towards the reaction components, that is to say which do not promote dimerisation of the ketene, and are liquid at the reaction temperature.

Solvents which may be mentioned as preferred are those from the series comprising hydrocarbons (aliphatics ($C_6$ to $C_{12}$), aromatics ($C_6$ to $C_{12}$) and alkylaromatics ($C_7$ to $C_{18}$)), halogenohydrocarbons, ethers and esters, for example petroleum fractions with boiling points from 130° C., toluene, ethylbenzene, cyclohexylbenzene, xylene, chlorobenzene, dichlorobenzene, trichlorobenzenes, methylnaphthalenes, biphenyl/diphenyl ether mixtures, dipropyl ether, dibutyl ether, ditolyl ether, ethyl acetate, butyl acetate and glycol methyl ether-acetate.

If the after-treatment of the primary product is to be carried out under normal pressure without intermediate isolation, solvents with a boiling point which is at least as high as the temperature to be applied during the after-treatment are advantageously employed.

It is also possible to use solvents with a lower boiling point if the reaction is carried out under pressure or the solvent is to be distilled off before or during the after-treatment of the primary product.

If isolation by aqueous alkaline extraction of the cinnamic acid formed is intended, the solvent used should have as complete as possible a miscibility gap with aqueous systems. Technical grade isomer mixtures of xylenes or dichlorobenzenes have proved advantageous.

The reaction according to the invention of benzaldehyde with ketene is in general carried out in the temperature range from −10° to +100° C., preferably from +20° to +70° C. In general, this reaction step is carried out under normal pressure. However, it is also possible to carry out the reaction under slightly reduced or increased pressure (for example in the pressure range from 500 mbar to 10 bar). Rapid and quantitative utilization of the ketene can frequently be promoted at a slightly increased pressure.

In a particular embodiment of the process according to the invention, the benzaldehyde is not reacted quantitatively but is preferably reacted only to the extent of 65 to 96%. The portion of the benzaldehyde which has not been consumed can be distilled off quantitatively during later working up and passed to a renewed reaction. The ketene utilization is virtually quantitative in a reaction procedure adapted in this manner.

The primary product obtained in the first reaction stage is split by means of heat in the second reaction stage.

The splitting is in general carried out in the temperature range from 100° to 250° C., preferably from 150° to 190° C.

The splitting is in general carried out under normal pressure. However, it is also possible to carry out the splitting under reduced or increased pressure (for example in the pressure range from 100 mbar to 25 bar).

The after-treatment according to the invention of the primary product is carried out in the presence of an acid or, preferably, basic catalyst.

Strong acids can be employed as acid catalysts for the splitting. Examples of strong acids which may be mentioned are: sulphuric acid, hydrogen chloride, hydrogen bromide, toluenesulphonic acid, pyridinium chloride and sodium bisulphate.

Examples of basic catalysts which can be employed are basic alkali metal or alkaline earth metal compounds, amines or aza compounds.

Examples of basic alkali metal or alkaline earth metal compounds are alkali metal and alkaline earth metal oxides and hydroxides, such as sodium hydroxide, potassium hydroxide, sodium hydroxide solution, potassium hydroxide solution, calcium oxide and calcium hydroxide, alkali metal carbonates, such as sodium carbonate and potassium carbonate, alkali metal salts of fatty acids, such as sodium acetate, sodium butyrate and sodium pivalate, and alcoholates, such as sodium methanolate and potassium isobutanolate.

Amines which may be mentioned are tertiary nitrogen bases, such as tributylamine, dimethylaniline and 4-dimethylaminopyridine.

Aza compounds can be, for example, diazabicyclononene and diazabicycloundecene.

Sodium hydroxide is preferably used as the basic catalyst.

The catalyst for the after-treatment of the primary product is in general used in an amount of 0.05 to 0.20 mol per mol of optionally substituted benzaldehyde employed.

In general, the after-treatment of the primary product is carried out in the same medium which has been used for the reaction of the optionally substituted benzaldehyde with the ketene. However, it is of course also possible to remove the solvent used in the first reaction stage and to use a different solvent for the second reaction stage or to carry out the reaction without a solvent.

The process according to the invention can be carried out either continuously or batchwise.

The process according to the invention can be carried out, for example, as follows: To form the primary product from the optionally substituted benzaldehyde and ketene, ketene gas is introduced, with effective distribution, into the benzaldehyde in question or the benzaldehyde solution in question in the presence of the catalyst according to the invention. The reaction has ended when the required amount of ketene has been consumed.

For carrying out the after-treatment of the primary product, the acid or basic catalyst is added and the mixture is heated to the desired splitting temperature.

The cinnamic acid formed can be isolated by customary techniques. It is possible to evaporate off the solvent and to purify the crude cinnamic acid which remains by recrystallization from water or suitable solvents. Equally, it is also possible for the crude cinnamic acid to be further processed directly, for example to cinnamic acid esters, which can then in turn be purified or used in a suitable manner. The following compounds, for example, can be advantageously prepared by this process variant: methyl, ethyl, propyl, isopropyl and butyl cinnamate. Extraction from the solvent phase with the aid of dilute aqueous alkali metal hydroxides or ammonia is frequently more advantageous. From the aqueous phase separated off, which contains alkali metal cinnamate or ammonium cinnamate, the cinnamic acid can be precipitated and separated out as crystals of outstanding quality by acidification with hydrochloric acid or sulphuric acid, if appropriate after passing the phase through a clarifying filter. Because of their purity, alkali metal or ammonium cinnamate solutions obtainable by this process variant can also be used for further reactions, for example for the preparation of phenylalanine, without intermediate isolation of the free acid.

The optionally substituted cinnamic acids prepared by the process according to the invention are in the trans form.

Cinnamic acids are obtained in high yields and high purity by the process according to the invention. Surprisingly, only very small amounts of by-products, such as styrene, are formed.

Cinnamic acid and its nuclear-substituted derivatives are industrially important starting materials for the preparation of biological and pharmaceutical active compounds, sweeteners, optical brighteners, liquid crystals and intermediates for numerous purposes (Ullmanns Encyklopädie der technischen Chemie (Ullmann's Encyclopaedia of Industrial Chemistry), 4th edition, Volume 24, page 592).

EXAMPLE 1

106 g of benzaldehyde are dissolved in 150 ml of toluene with 2 g of zinc acetate dihydrate and 1.5 ml of acetic acid in a stirred apparatus, under a nitrogen atmosphere. Ketene gas, which can easily be produced on a laboratory scale by splitting of diketene by means of heat (compare Houben-Weyl, Volume VII/4, page 80; and Org. Syntheses. Coll. Vol. V, page 679) is passed into this solution at 30° to 40° C. in the course of 3 to 4 hours. When 92 to 96% of the benzaldehyde has reacted, determined by analysis by gas chromatography, the addition of ketene is interrupted and the reaction mixture is subsequently stirred for a further brief period and transferred to a VA steel low-pressure autoclave. 4 g of 92% pure sodium hydroxide powder are added and the toluene and excess benzaldehyde are distilled off over a descending condenser into a receiver. The viscous, light-colored residue is then heated at 180° C. for 1 hour and, after cooling to about 100° C., the resulting reaction product is taken up in 700 ml of water and dissolved by adding 140 ml of 20% strength ammonia. After addition of about 20 g of active charcoal, the mixture is stirred at 60° to 70° C. for a further brief period and clarified by filtration and the filtrate is acidified with 30% strength hydrochloric acid until it gives a clearly acid reaction. Cinnamic acid thereby precipitates in white crystals, which are filtered off with suction, washed with a little acidified cold water and dried at 70° C. in a drying cabinet.

Yield: 109 g of colorless crystalline cinnamic acid of melting point 133° to 134° C.; taking into consideration the 8.5 g of reusable benzaldehyde in the toluene distillate (determined by gas chromatography), the yield is 80.2% of theory.

If, instead of zinc acetate, the equimolar amount of zinc isobutyrate or zinc pivalate or zinc propionate is used, similarly good yields are obtained with the same outstanding product quality.

EXAMPLE 2

2 g of zinc acetate dihydrate and 2 ml of glacial acetic acid are added to a solution, prepared under a nitrogen atmosphere, of 106 g of benzaldehyde in 120 ml of dichlorobenzene. Ketene gas is passed in, with stirring, during which the temperature is allowed to rise from about 20° to 40° C. After about 94% of the benzaldehyde has reacted (according to determination by gas chromatography), the mixture is subsequently stirred at 40° C. for a further 30 minutes.

The introduction of the ketene lasts about 4 hours; the reaction time can be reduced to about half by external cooling. Thereafter, 4 g of sodium hydroxide powder are added and the mixture is heated to 180° C. After being stirred at this temperature for half an hour, it is allowed to cool to 100° C. and 700 ml of water and 140 ml of concentrated aqueous ammonia are allowed to run in. The mixture is stirred at 60° C. for half an hour, the phases are allowed to settle, the (lower) dichlorobenzene phase is removed and the aqueous phase is clarified by filtration, using 10 g of active charcoal. The resulting water-clear filtrate is acidified and the crystalline cinnamic acid which has precipitated is filtered off with suction, washed with a little cold water and dried in a drying cabinet at 70° C.

Yield: 120.2 g; white crystals of melting point 133° to 134° C.; content: 99.5%=86% of theory, taking into consideration 6.3 g of recovered benzaldehyde. After replacing the benzaldehyde consumed and drying, the chlorobenzene phase can be used again in the ketene addition reaction. If, instead of the zinc acetate, the same amount of iron acetate is used, cinnamic acid with a similarly good product quality is obtained in a yield of 79% of theory.

Similarly high yields (84 to 86% of theory) are achieved with zinc propionate, zinc butyrate, zinc isobutyrate, zinc pivalate and zinc isovalerate instead of zinc acetate.

Cinnamic acid yields of 76 to 80% of theory are obtained with zinc stearate, zinc benzoate, zinc hexahydrobenzoate and zinc cinnamate as catalysts.

EXAMPLE 3

212 g of benzaldehyde are stirred with 4 g of zinc acetate dihydrate and 4 ml of glacial acetic acid under a nitrogen atmosphere. A total of 70 g of ketene are passed into the mixture in the course of 4 hours, starting at 20° C. and rising to 40° C., and the mixture is then subsequently stirred at 40° C. for a further 30 minutes. Thereafter, 5 g of sodium hydroxide powder are added to the reaction mixture and the mixture is gradually heated up to 180° C., with stirring, excess benzaldehyde, contaminated with a little styrene, being distilled off—under somewhat reduced pressure. The distillate consists of 25 g of benzaldehyde and 15.3 g of styrene (total: 67.9 g) and can, according to its benzaldehyde content, be employed again without the styrene having to be removed.

The residue is stirred at 180° C. for 1 hour. After the temperature has fallen to about 100° C., 0.75 l of water and 145 ml of concentrated aqueous ammonia are allowed to run in. The mixture is stirred at 70° to 80° C. until solution is complete, 20 g of active charcoal are then added and the mixture is filtered.

The water-clear filtrate is acidified with 30% strength hydrochloric acid and the cinnamic acid which has precipitated is filtered off with suction at room temperature, washed with a little cold water and dried in a drying cabinet at 60° to 70° C. Yield: 201.3 g; white crystals, melting point 133° to 134° C.; content: 99%=89.2% of theory, based on the benzaldehyde reacted.

EXAMPLE 4

If the procedure followed is as described in Example 2, but the following basic or acid catalysts are employed instead of sodium hydroxide in the after-treatment of the primary product, the non-optimized yields of cinnamic acid listed in the table are obtained:

| Catalyst | Yield (% of theory) | Amount of catalyst [g] |
| --- | --- | --- |
| a Potassium hydroxide powder | 84 | 4 |
| b Calcium hydroxide powder | 62 | 5 |
| c Anhydrous sodium acetate | 77 | 5 |
| d 4-Dimethylaminopyridine | 83 | 3 |
| e Tributylamine | 68 | 4 |
| f Diazabicyclononene | 84 | 4 |
| g Diazabicycloundecene | 82 | 4 |
| h Sulphuric acid | 78 | 6 |
| i Hydrogen chloride gas | 80 | 8 |
| k Toluenesulphonic acid | 64 | 5 |

EXAMPLE 5

140 g of 4-chlorobenzaldehyde are dissolved in 100 ml of dichlorobenzene together with 2 g of zinc acetate and 2 ml of acetic acid. Ketene gas is passed in at 30° to 40° C. until 90% of the 4-chlorobenzaldehyde has reacted. Thereafter, 3 g of sodium hydroxide powder are added and the mixture is heated at 180° C. for 1 hour, allowed to cool to 120° C. and poured into 600 ml of water and 120 ml of concentrated ammonia with stirring. After the mixture has been subsequently stirred for half an hour, the aqueous phase is separated off from the dichlorobenzene phase and clarified with the addition of 20 g of active charcoal, and the clear filtrate is acidified with hydrochloric acid. The 4-chlorocinnamic acid which precipitates as white crystals is filtered off with suction, washed with a little cold water and dried.

According to determination by gas chromatography, the dichlorobenzene phase contains 12 g of reusable 4-chlorobenzaldehyde.

Yield: 121 g of 4-chloro-cinnamic acid, colorless crystals of melting point 248° to 250° C.;=72.5% of theory, based on the 4-chlorobenzaldehyde reacted.

The following substituted cinnamic acids can be obtained with in each case the melting points given in the table from the relevant aldehydes in a corresponding manner.

| Example | Cinnamic acid derivative | Melting point |
| --- | --- | --- |
| 6 | 4-Methyl-cinnamic acid | 197–198° |
| 7 | 2-Fluoro-cinnamic acid | 176–178° |
| 8 | 4-Methoxy-cinnamic acid | 172/191° |
| 9 | 3-Nitro-cinnamic acid | 200–202° |
| 10 | 4-Phenyl-cinnamic acid | 222° |
| 11 | 3,4-Methylenedioxy-cinnamic acid | 238° |
| 12 | 2-Chloro-5-nitro-cinnamic acid | 219–220° |
| 13 | 2,4-Dichloro-cinnamic acid | 229–231° |
| 14 | 4-Bromo-cinnamic acid | 249–251° |

It will be understood that the specification and examples are illustrative but not limitative of the present invention and that other embodiments within the spirit and scope of the invention will suggest themselves to those skilled in the art.

We claim:

1. In the preparation of a cinnamic acid by reacting the corresponding benzaldehyde with ketene in the presence of a catalyst, the improvement which comprises using as the catalyst an iron and/or zinc salt of a mono- or di-carboxylic acid with 2 to 20 carbon atoms containing free carboxylic acid and/or anhydride, and then splitting the reaction product in the temperature range from 100° to 250° C. with an acid or basic catalyst.

2. A process according to claim 1, wherein 0.1 to 10 mol % of the catalyst, based on the benzaldehyde, is employed.

3. A process according to claim 1, wherein the reaction is carried out in a solvent.

4. A process according to claim 1, wherein the reaction with ketene is carried out in a temperature range from −10° to +100° C.

5. A process according to claim 1, wherein the acid or basic catalyst is an alkali metal compound, alkaline earth metal compound, amine or aza compound.

6. A process according to claim 1, wherein the acid or basic catalyst is a strong acid.

7. A process according to claim 1, wherein 0.05 to 0.20 mol of the acid or basic catalyst is used per mol of the benzaldehyde.

8. A process according to claim 1, wherein the iron and/or zinc salt contains 1 to 80% by weight of free carboxylic acid and/or anhydride.

9. A process according to claim 1, wherein the free acid is of the formula

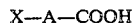

in which
X denotes carboxyl or hydrogen and
A can denote a divalent radical which is derived from the group comprising saturated or unsaturated aliphatic hydrocarbons with 1 to 18 carbon atoms, cycloaliphatic hydrocarbons with 5 to 12 carbon atoms, araliphatic hydrocarbons with 7 to 18 carbon atoms or aromatic hydrocarbons with 6 to 12 carbon atoms and, if X represents a carboxyl group, also a single bond.

10. A process according to claim 1, wherein the benzaldehyde is of the formula

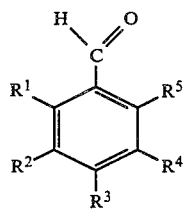

in which
$R^1$ to $R^5$ are identical or different and denote hydrogen, halogen, hydroxyl, nitro, lower alkyl, lower alkoxy or optionally substituted phenyl, it being possible for an aromatic ring to be fused onto two adjacent radicals, or it being possible for two adjacent radicals to be connected by the group

—O—CH$_2$—O—, and at least one of $R^1$ and $R^5$ is hydrogen.

11. A process according to claim 7, wherein the reaction with ketene is carried out in a solvent in a temperature range from 20° to 70° C. in the presence of 0.5 to 4 mol % of the iron and/or zinc salt based on the benzaldehyde, the salt containing 1 to 50% by weight of an acid of the formula

H—B—COOH, in which
B is a divalent radical from the group comprising saturated aliphatic radicals with 1 to 12 carbon atoms, cycloaliphatic radicals with 5 or 6 carbon atoms, araliphatic radicals with 7 to 9 carbon atoms and aromatic radicals with 6 to 10 carbon atoms, the benzaldehyde is of the formula

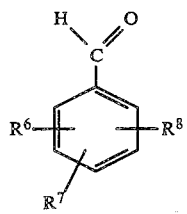

in which
at least one ortho-position is unsubstituted, and
$R^6$ to $R^8$ are identical or different and denote hydrogen, fluorine, chlorine, bromine, nitro, methyl, ethyl, methoxy, ethoxy or phenyl, it being possible for two adjacent radicals to be connected by the group

—O—CH$_2$—O—, and the acid or basic catalyst is a strong acid, an alkali metal compound, alkaline earth metal compound, amine or aza compound.

* * * * *